United States Patent [19]
Churchill et al.

[11] Patent Number: 6,001,060
[45] Date of Patent: Dec. 14, 1999

[54] VIDEO DATA REPRESENTATION OF PHYSIOLOGICAL DATA

[75] Inventors: Bernard M. Churchill; Edward F. Wahl, both of Pacific Palisades, Calif.

[73] Assignee: Regents of the University of California, Oakland, Calif.

[21] Appl. No.: 08/865,774

[22] Filed: May 30, 1997

Related U.S. Application Data

[60] Provisional application No. 60/019,146, Jun. 4, 1996.

[51] Int. Cl.⁶ ........................................ A61B 5/00
[52] U.S. Cl. ........................................... 600/300
[58] Field of Search ..................... 395/140, 141, 395/133; 600/300, 301, 398, 400, 440, 443, 453, 546; 128/920–924, 898, 897

[56] References Cited

U.S. PATENT DOCUMENTS

| | | | |
|---|---|---|---|
| 5,165,410 | 11/1992 | Warne et al. | 600/425 |
| 5,255,187 | 10/1993 | Sorensen | 128/923 X |
| 5,287,273 | 2/1994 | Kupfer et al. | 600/431 |
| 5,331,548 | 7/1994 | Rollema et al. | 600/561 |
| 5,423,329 | 6/1995 | Ergas | 600/546 |
| 5,503,986 | 4/1996 | Steers et al. | 435/7.92 |
| 5,517,251 | 5/1996 | Rector et al. | 348/476 |
| 5,657,759 | 8/1997 | Essen-Moller | 600/431 |
| 5,772,584 | 6/1998 | Davies | 600/300 |
| 5,800,347 | 9/1998 | Skates et al. | 600/300 |
| 5,807,256 | 9/1998 | Taguchi et al. | 600/425 |

*Primary Examiner*—Samuel Gilbert
*Attorney, Agent, or Firm*—Oppenheimer, Wolff & Donnelly, LLP

[57] ABSTRACT

A system for patient diagnostic testing includes the physiological data output is in a two dimensional graphical format. Optionally, the report includes imaging data. Color is a dimension provided to the graphical presentation of normal patient data in horizontal and vertical dimensions. Detrusor pressures are obtained. One detrusor pressure is the difference between average data points of the bladder and rectal pressures. The other is obtained by subtracting curve fitted rectal and bladder pressures. The displayed data is a presentation including bladder capacity information, pressure characteristics, and data as a function of volume such that bladder volume is indicated.

18 Claims, 10 Drawing Sheets

VIDEO DATA REPRESENTATION OF PHYSIOLOGICAL DATA

This application claims benefit of provisional application No. 60/019,146 filed Jun. 4, 1996.

BACKGROUND

This invention is directed to a specific software program for use in recording and displaying physiological data. More particularly the invention is directed to video urodynamics diagnostic testing.

To collect urodynamic test data of sufficient accuracy and to generate a report of the required quality it is necessary to have a system that would produce such a product. Different existing software, application programs, existing systems are unacceptable. Further the modification of existing urodynamic systems were also unacceptable.

There are currently two approaches to the use of computers in operations. The first approach uses a dedicated computer. This which may in fact not appear to be a computer at all, but simply is contained in a black box with the usual operating devices. These are triggers and switches that an operator may need to carry out a particular function. Such computers are generally controlled by dedicated software systems that provide simple operator interfaces specific to the task at hand.

In such operations the operator maintains the usual skill of their particular trade or profession and the computer is merely there as an adjunct. The operator's attention is focused on the particular operation at hand and not on the operation of the computer. This means that the particular software system and computer cannot be used by other companies that might have a slightly different configuration. Each particular type of industry would have particular specialized software programs specifically for it's functions.

The second approach to the use of computers is a computer system which includes a number of application programs which can be used to do a multitude of tasks and do them in a variety of ways. In such operations of the computer becomes very labor-intensive and requires a skilled computer operator. If a task is repetitive then the use of a specialized operation is inefficient.

It is necessary to have a simple approach that will allow the operator to concentrate on the patient and test at hand, rather than going through a menu to achieve a particular function.

In the actual operation of a clinic there is only one particular set of sequences that will ever be used routinely. These functions should be clearly set up in a simple key sequence for the operators. This allows the operator to perform in the most efficient way and concentrate on the task at hand.

This invention provides for a dedicated diagnostic product and method for use in recording physiological data in an improved manner.

SUMMARY

A system for patient diagnostic testing includes the physiological data output is in a two dimensional graphical format. Optionally, the report includes imaging data. Color is an added dimension provided to the graphical presentation of normal patient data. The color is preferably in horizontal and vertical dimensions. In other situations the color can be in different dimensions on the two dimensional graphical output of the normal data.

According to the invention there is provided a specific software program for use in recording and displaying physiological data. Preferably this data is urodynamic.

The invention provides for video urodynamics diagnostic testing. The data output is the production of a high quality presentation report of the physiologic data and the imaging data. Use is made of color as a third dimension to that of the two normal horizontal and vertical dimensions on a sheet of paper. Preferably the colors of green, yellow and red that are commonly used for safe, danger and caution are employed.

A software program reads the data produced from an analog to digital converter (A to D unit) at a rapid rate. Preferably the rate is approximately 100 samples per second. The input is processed in an inventive manner to eliminate artifacts or spikes in the data that are non physiologic and still retain physiologic data.

The data is preferably further processed so as to minimize noise by using appropriate smoothing functions. This data is then stored and subsequently processed by the second piece of software which performs further curve fitting and data smoothing to produce the quality result desired. The methods for processing and interpreting the data and handling it to produce the final output result are specifically for this program for this particular physiologic test.

Another inventive feature of the program is that it presents the physiologic data in an inventive way that has not been previously done. By this data display and printing procedure the data is easily interpreted.

Specifically, the presentation includes the bladder capacity information on the chart as vertical lines. Secondly, it includes the safe pressure as horizontal lines, that is the color lines. Thirdly, it presents the data as a function of volume so that the bladder volume can be indicated on the chart. It has been determined that it is more relevant to know the pressures as a function of volume in the bladder than it is to know the pressure as a function of time which is the normal way of presenting the data.

The invention is further described with reference to the accompanying drawings.

DRAWINGS

The present invention, both as to its organization and manner of operation, together with further objects and advantages thereof, may best be understood with reference to the following description, taken in connection with the accompanying drawings in which.

DESCRIPTION

A system for patient diagnostic testing includes the physiological data output in a two dimensional graphical format. Color is a dimension provided to the graphical presentation of normal patient data in horizontal and vertical dimensions. Color is optional, however the data represented by the different colors or different zones imparts information or data which essentially provides another dimension to the diagnostic report.

In some applications, the report includes imaging data. The diagnostic testing report is a data output of a specific patient. It comprises, on a single report, at least a two dimensional graphical presentation of the physiologic data of the patient. There is also in an, at least, two dimensional graphic format the data of an individual's physiologic normals for the specific patient.

By this "normal data" is meant the normal data of a specific healthy individual having the same characteristics as the specific patient in the sense, for instance, of sex, age, height, weight and other important characteristics. This data of the normal individual is obtained from standard references, and is input into the report to be a two dimensional graphical format of that data. This is the data that is represented in color or different zones. For each characteristic of normal standard the particular zones or colors will vary in their presentation. Thus for a child the amount of red/yellow/green (or the size of each respective zone as may be represented by each color) will be different relative to the normal for an adult and different adults. Additionally, vertical lines and other data on the clients would vary for the normal of each specific patient.

Accordingly the colored or different zone areas define information or data providing the background against which the patient data is to be evaluated. The zones therefore provide for a summation or compression of different data from normal subjects against which the patient is evaluated or diagnosed. The patient's data is preferably superimposed on the background of color or different zones of normal data, so that on a single reading a diagnostician can evaluate the patient quickly and easily. In some cases the patient data can be set alongside the normal subject data in the report. This will provide yet a different form of presentation of the data.

The data output is a specialized type which is essentially not compatible with the output of prior existing programs. The data output includes a combination of x-rays and other physiological data. A fundamental programming level produces the precise data product, and is able to handle the input data in the simplest form possible consistent with the repetitive operation applicable to a diagnostic test configuration.

The System

A specific software program permits recording and displaying urodynamic data to permit for diagnostic testing.

The data output is the production of a high quality presentation report of the urodynamic data and the X-ray imaging data. The colors of green, yellow and red are employed as the background on which the data is displayed. The presentation includes the bladder capacity information on the chart as vertical lines. The safe pressure are horizontal lines, that is the colored areas or lines. The bladder volume can be indicated on the chart.

A software program reads the data produced from an analog to digital converter (A to D unit) at a rate of approximately 100 samples per second. The input is processed to eliminate artifacts or spikes in the data that are non physiologic and still retain physiologic data. The data is processed so as to minimize noise by using appropriate smoothing functions. This data is then stored and subsequently processed by the second piece of software which performs further curve fitting and data smoothing to produce the quality result desired.

The Software Program

The software program consists of three main sub-programs, each considered an individual program. The three programs are first the input routine, second real time data collection analysis and processing program and third, post test data analysis, processing and presentation.

Figure 1:
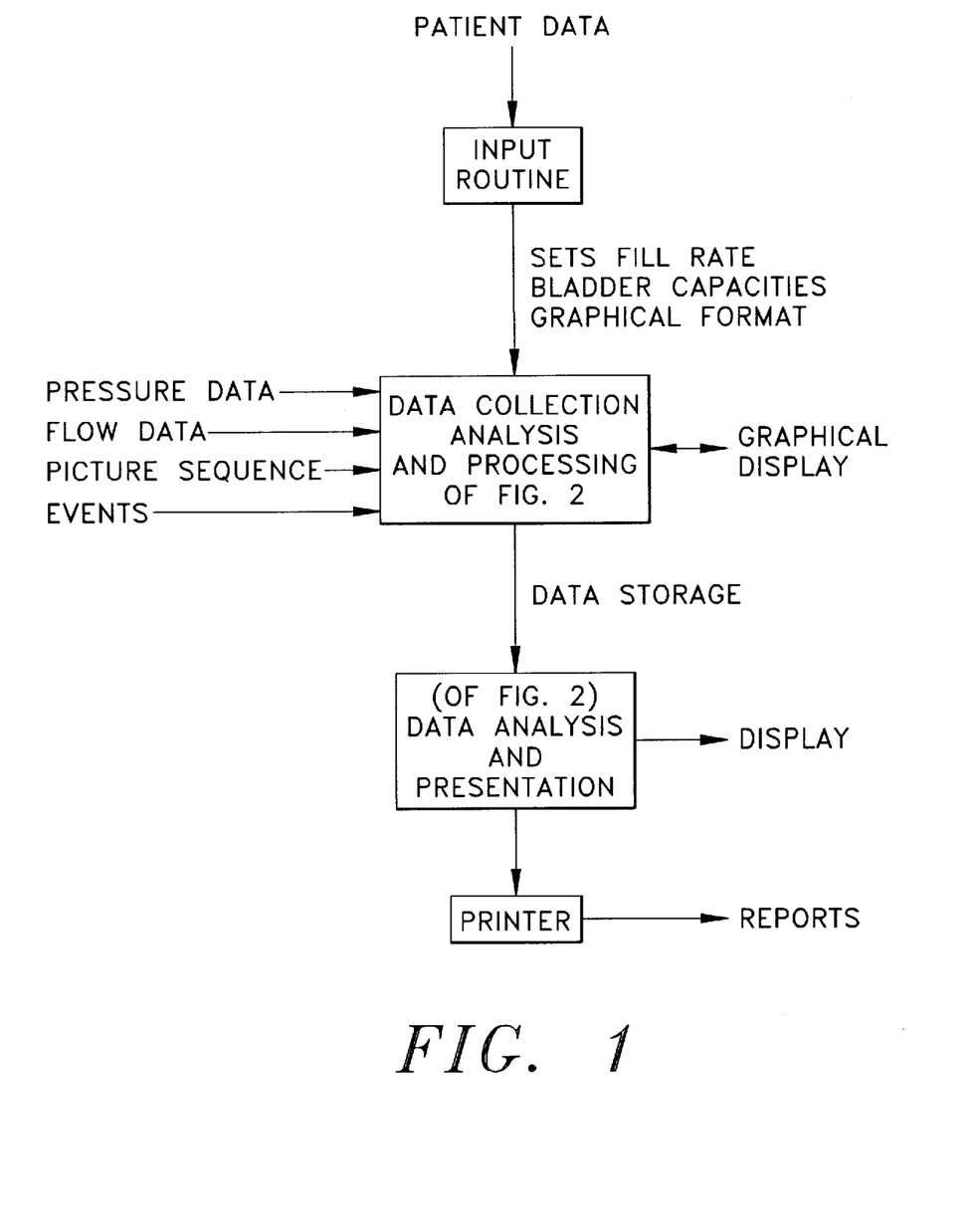
FIG. 1 is a flow diagram representation of the overall program flow.
Figure 6:
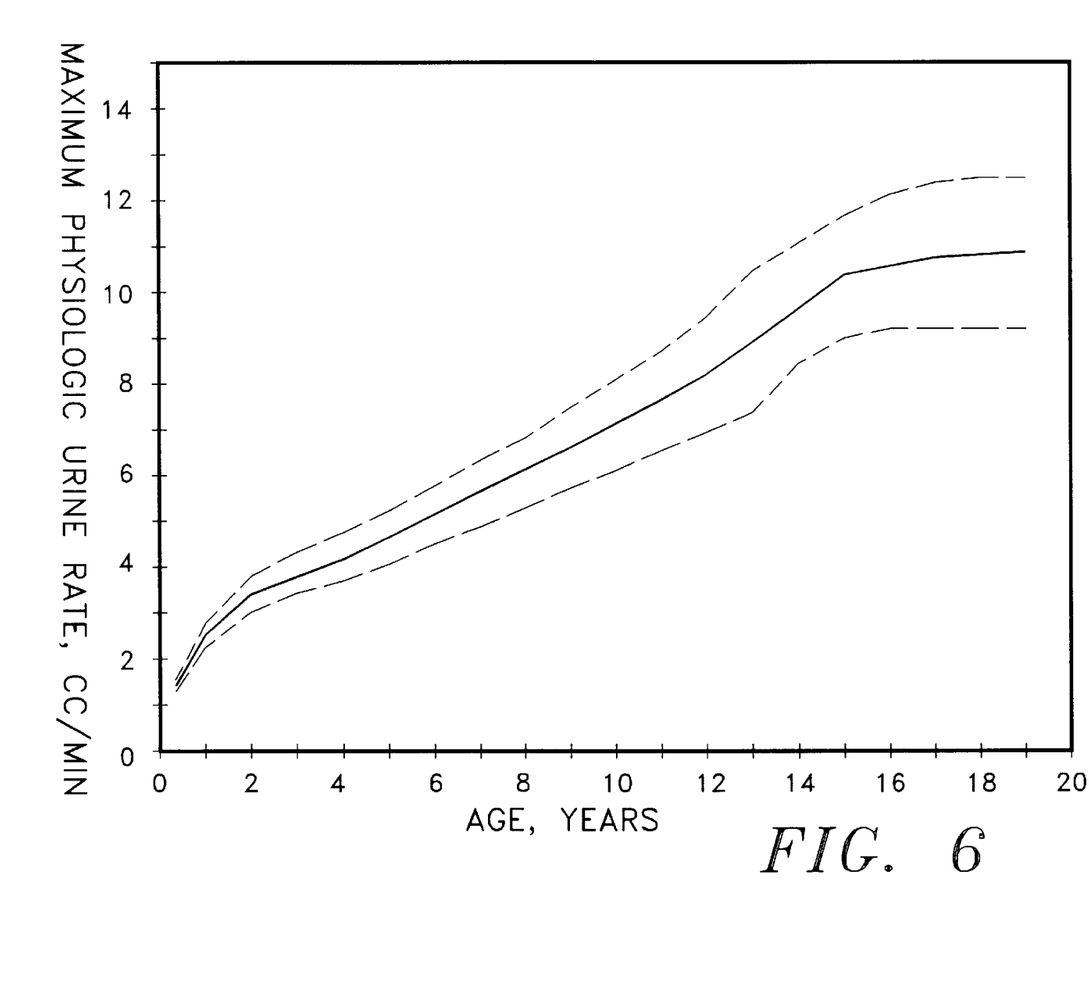
FIG. 6 is a graphical representation of data relating the urine rate relative to age of a patient.

This is shown schematically in FIG. 1 together with the significant input and output features of each of the main sub programs. The first input routine takes the patient data and calculates the characteristics necessary for the display. This is the bladder capacities and fill rates to be used based on mathematical algorithms relating these physiological parameters derived from the data as represented in FIG. 6. The second program, the real time data collection analysis and display program utilizes specialized hardware in conjunction with the software described below to provide the graphical display. In addition, that program stores the data for subsequent analysis.

Finally, the data analysis and presentation program takes the stored data and performs further analysis to yield the highest quality and most easily interpreted report. In addition, it integrates the x-ray data. This then is sent to a printer and the reports are presented. The data can display the information at various locations such as in the clinic, office or consultation office for discussion purposes.

Figure 9:
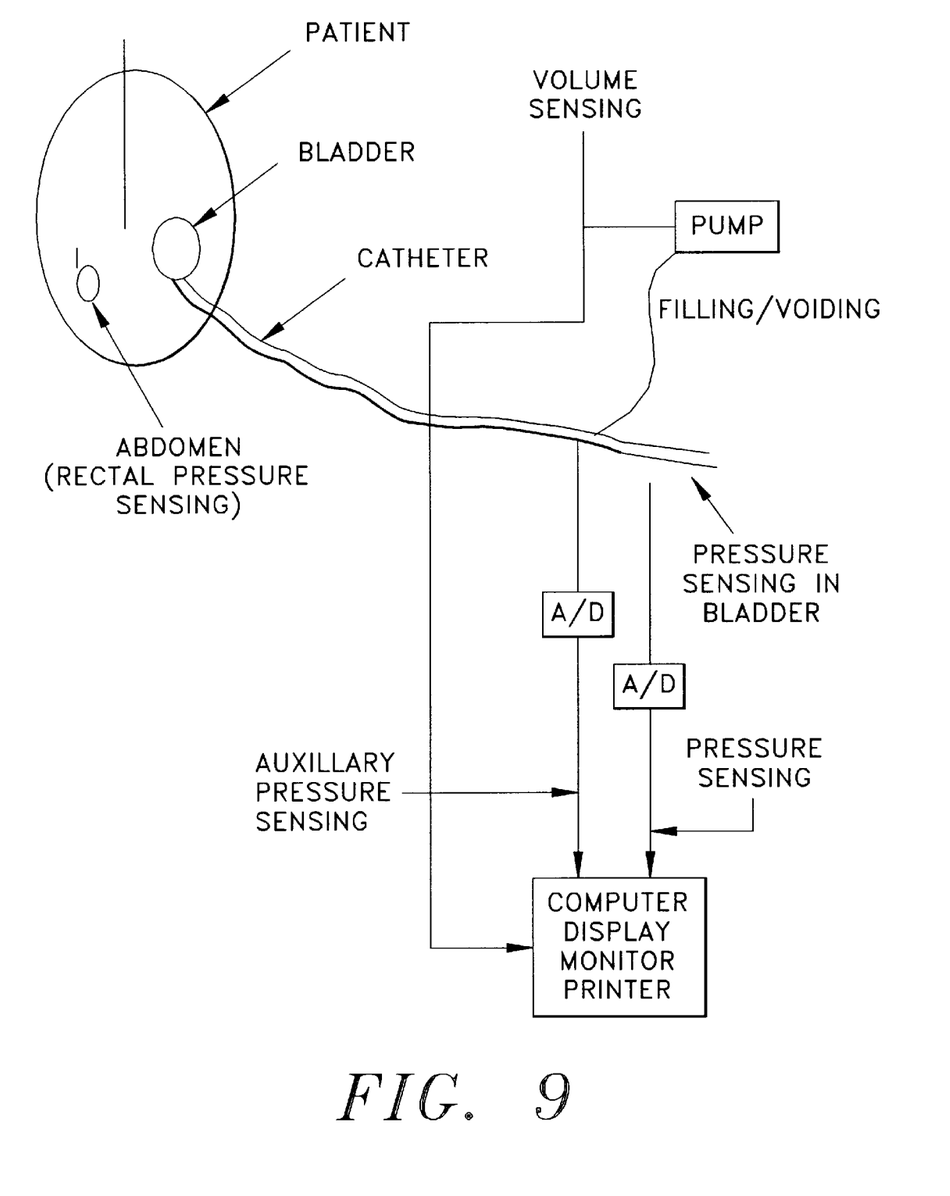
FIG. 9 is a representation of a catheter in location in a bladder and a pressure sensor for the abdominal area outside the bladder.

As shown in FIG. 9 there is represented a patient, the patient's bladder and abdomen. A catheter is directed into the bladder with three pipes. One pipe is for filling the bladder with fluid, another pipe is for measuring the bladder pressure, and the third pipe is an extra. There is also a sensor located in the abdomen for measuring the pressure in the abdomen, namely in the area outside the bladder. Outputs from the fluid filling pipe and the two pressure sensors are directed to the computer unit or hardware which is used for displaying, outputting or printing the results.

Real Time Data Analysis and Interpretation Program

Using appropriate hardware and a data sampling rate of approximately 100 samples per second, highly accurate data is provided to the computer memory for analysis, recording and display.

Figure 2:
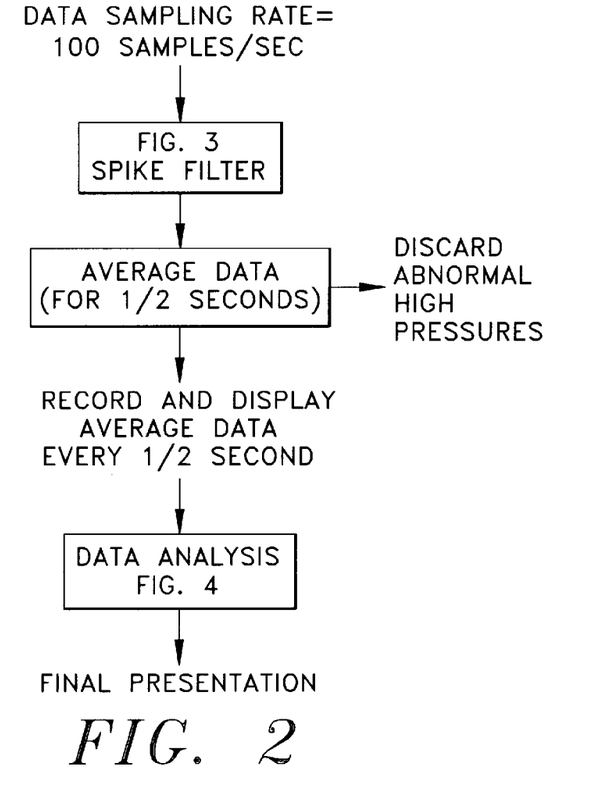
FIG. 2 is a flow diagram representation of the general data analysis and interpretation.

As shown in FIG. 2, this data first goes through a spike filter to discard abnormally high pressures and then the data is averaged which is recorded and displayed every ½ second. Subsequent data analysis is performed to provide the final presentation as shown.

The spike filter functions as follows. If the rate of rise of the pressure is so rapid that it exceeds a pre-set value that data is discarded and/or if the pressure exceeds the average pressure that has been maintained over a recent time period, such as 5 seconds, or by more than a pre-set amount, for example 10%, then again, that data is discarded. This provides a means to remove data that is a result of artifacts such as patient coughing or crying that would distort the data.

In addition, if the technician wishes to check to make sure the pressures are being properly transmitted from the patient to the computer, then if pressure is applied to the abdomen and this causes a spike, again the spike would be removed by this procedure and not bias the data. After the spiked data has been removed, the data is then averaged over a 1½ second period. The time need not be precisely ½ second but something of the order of this time period is convenient for this type of physiological activity.

The key pressure parameter that is presented is the detrusor pressure. The detrusor pressure is defined to be the difference between the bladder pressure which is experimentally measured or the rectal pressure in the abdomen which is also experimentally measured. If a detrusor pressure is obtained by subtracting the directly measured bladder and rectal pressures, then any noise in those pressures could be magnified in calculating the detrusor pressure. This is particularly true if they are out of phase which can frequently happen during the testing. A better result is obtained by first smoothing the bladder pressure data and the rectal pressure data in the abdomen and then perform the subtraction to obtain the detrusor pressure. This is the procedure that is followed by this software program.

The graphical presentation contains two detrusor pressures which are displayed. One detrusor pressure is that which is the difference between the ½ second average data points of the bladder and rectal pressures. The other pressure is that which is obtained by subtracting curve fitted rectal and bladder pressures. This gives a particularly smooth non-noisy detrusor pressure and is the pressure that is used to determine when the detrusor pressure changes from the green zone to the yellow zone and so on. The method by which these smooth rectal and bladder pressures are calculated is discussed below in the next section.

Post Test Data Analysis

Curve fitting the rectal and bladder pressures is accomplished by fitting these curves over a variable time period or number of data sample points. A useful range turns out to be between 10 and 500 seconds. This variation can be chosen depending upon the particular nature of the test and the characteristic of the patient in order to produce the best result or a variety of results.

Figure 3:
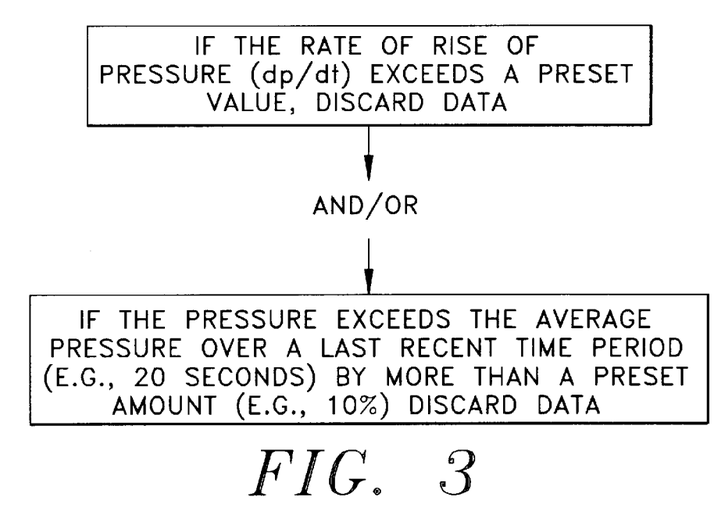
FIG. 3 is a flow diagram representation of the spike filter.
Figure 4:
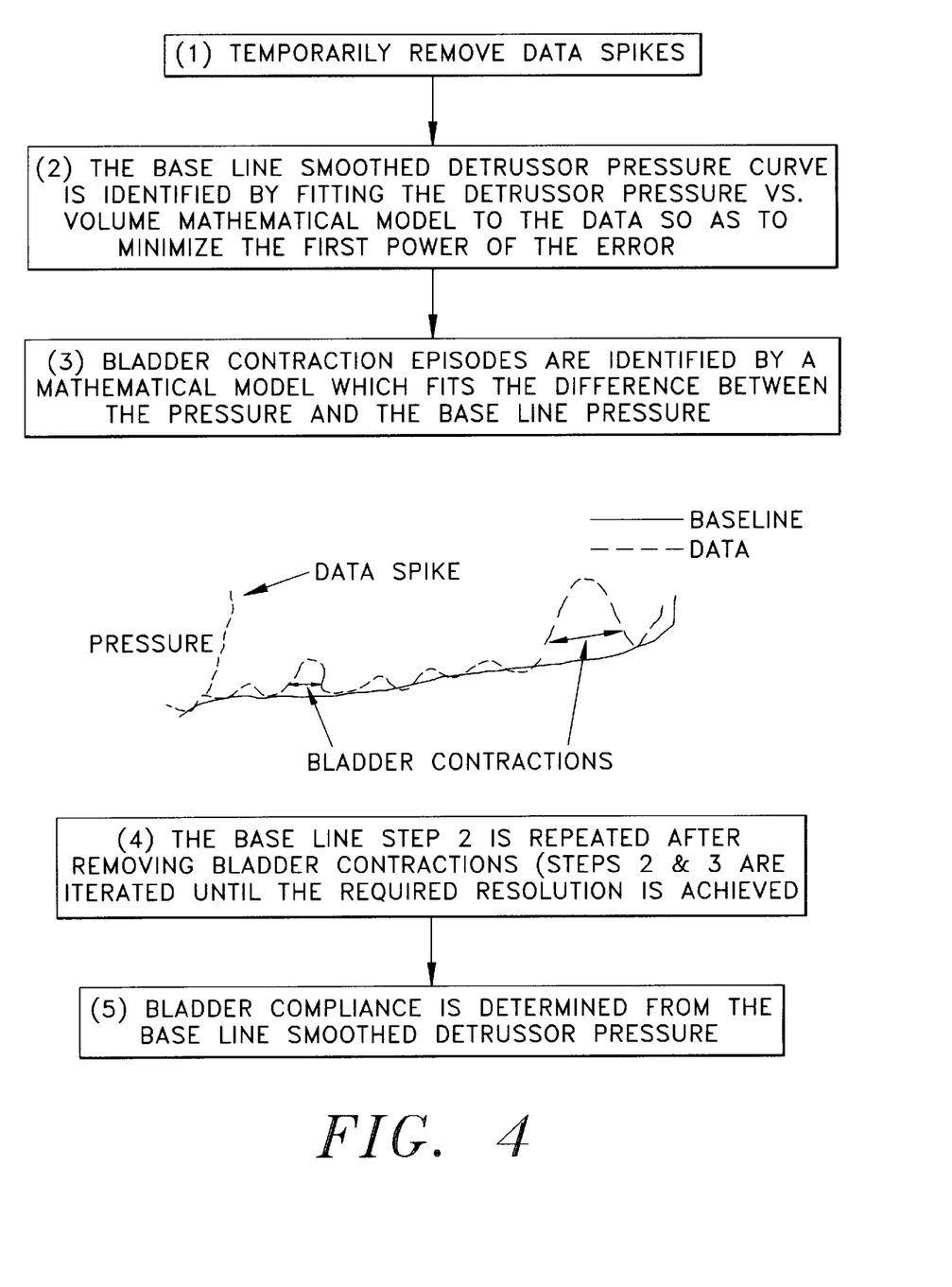
FIG. 4 is a flow diagram representation of the curve smoothing.
Figure 5:
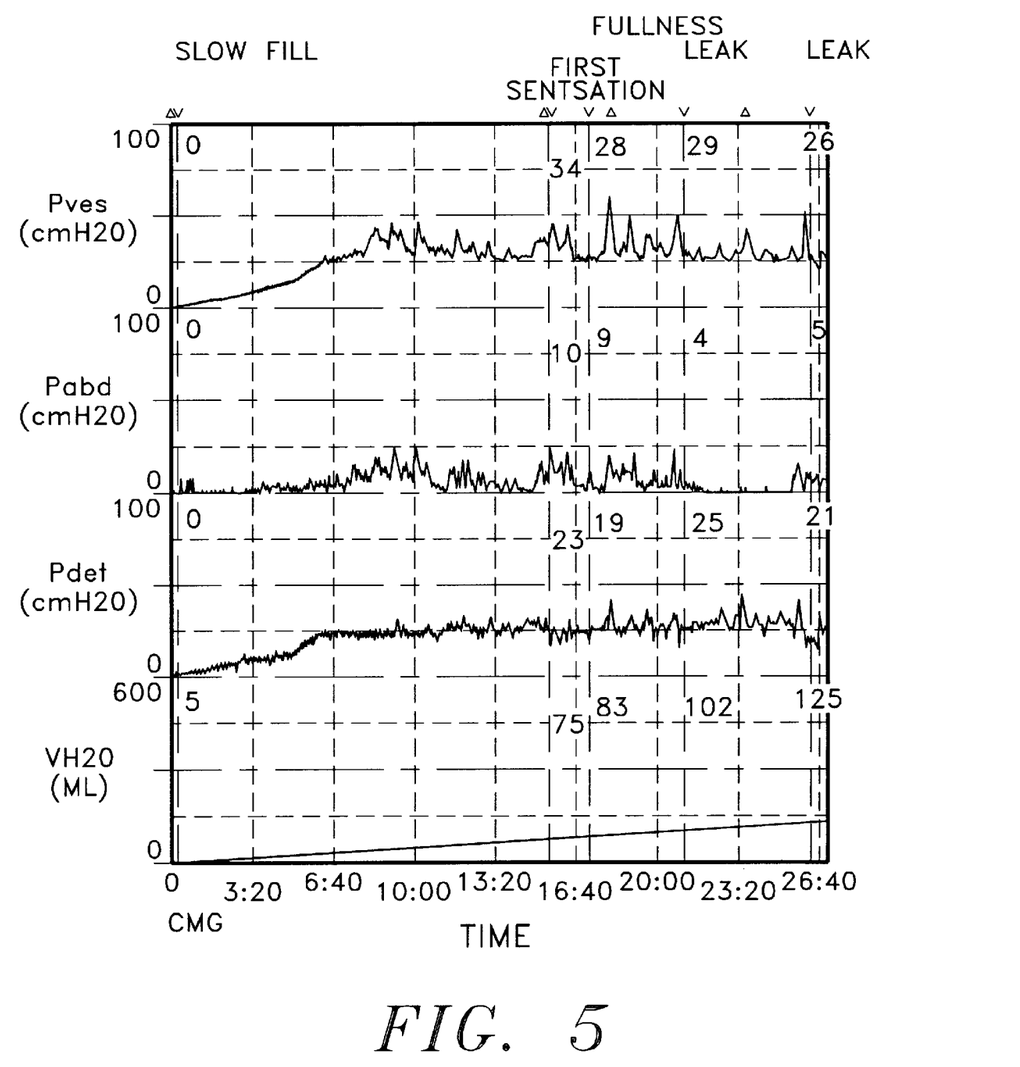
FIG. 5 is a three part graphical representation of the prior art system of data output. This system has three data graphs all of which show different values in relation to time.

These smooth rectal and bladder pressure data lines are then subtracted in order to obtain smooth detrusor pressure curves. The procedure by which the detrusor pressure curve is then fitted is as follows:

1. The baseline smooth detrusor pressure curve is identified by fitting the detrusor pressure versus volume mathematical model to the data so as to minimize the first power of the error. This is done after temporarily removing any data spikes.
2. The bladder contraction episodes are then identified by mathematical models which fits the difference between the pressure and the baseline pressure as shown in FIG. 3.
3. The baseline step 1 above is repeated after removing the bladder contractions. Then steps 1 and 2 can be repeated until the required resolution is achieved to obtain the best baseline detrusor pressure curve.
4. The bladder compliance is then determined from the baseline smooth detrusor pressure according to specific algorithms incorporated in the software.
5. The magnitude of the bladder contractions can then be determined by integrating the curve of the bladder contraction, that is the difference between the bladder contraction, determining the area of the bladder contraction curve less that of the detrusor baseline curve as shown in FIG. 5. The other parameters that are determined are the height of the bladder contraction. Infusion rates chosen for urodynamic testing in children are based on fixed values or patient age, not on physiologic data related to in vivo bladder filling. This current strategy can induce artifact as pediatric bladders are filled at rates much faster than in even the most extreme diuretic conditions. An infusion rate is used that mimics more closely urinary flow rates based on a patient's size and age-adjusted GFR. An obligatory 80% of the kidney's GFR is reabsorbed in the proximal tubule, and, thus, only 20% of the GFR is available as potential urine (Guyton, 1975). In extreme conditions, i.e. post renal transplant, the maximum urine output that the lower urinary tract will be challenged with is approximately 10% of the patient's size and age-adjusted GFR. A CMG infusion rate based on this value for the following reasons: (a) it is physiologic, rather than empiric, (b) it is based on child size in addition to age, and (c) the rate of development of two closely linked physiologic parameters, GFR and pressure-specific bladder capacity, is the same. This is demonstrated in FIG. 6. The solid line depicts the mean 10% of GFR (left vertical axis) versus age. The dotted lines depict the mean bladder volume (right vertical axis) versus age. As demonstrated, the rate of development of the GFR and bladder volume, as reflected by the slope of the two curves, is almost identical. Based on this information, a mathematical algorithm for recommended infusion rates to be used in bladder filling during urodynamic studies and the minimum and mean bladder capacities are provided in the program.
6. Bladder compliance is determined from the baseline smooth detrusor pressure curve according to the algorithms of FIG. 6.

These curve fitting techniques are incorporated to a limited extent in the real time data program in order to improve the real time presentation.

Incorporation of X-ray Data Into Data Output Report

The x-ray data which has been obtained during the test is stored in digital format. This is for example by a Phillips x-ray unit. This data is then transferred either electronically or manually by a data cartridge or tape into the data analysis computer. This data is then read and using a proprietary program is converted into an appropriate format so that it can be sent to a printer.

The particular software for producing this image on the printer to the best resolution is a uniquely developed program specific for this purpose. That is, it is specific for transferring x-ray digital data of a particular format into the best quality x-ray image using existing printer technology. Specifically, each piece of digital data that describes the x-ray image consists of a single number in this case, that varies between 0 and 255. The value of the number indicates the amount of grayness of the image. The image consists of 512 of these data values in each of 512 rows. Thus, the image is made up of a matrix array of 512×512 data values each varying between 0 and 255 to indicate the amount of grayness or blackness of each particular matrix location. Some x-ray images are 1024×1024 pixels, the exact number is not important.

Many software application programs exist for taking x-ray images and various kinds of images and printing them out on printers. These various programs will produce various quality results. The purpose of the invented software program is to take this data image and to produce the best possible result with specific printers.

Features of the Video Urodynamics Data Output

The advantages of the invented data output is a report that is graphic, comprehensive, provides simultaneous physiological and anatomical imaging, provides individualized normals and provides only the physiologically significant data.

Figure 7:
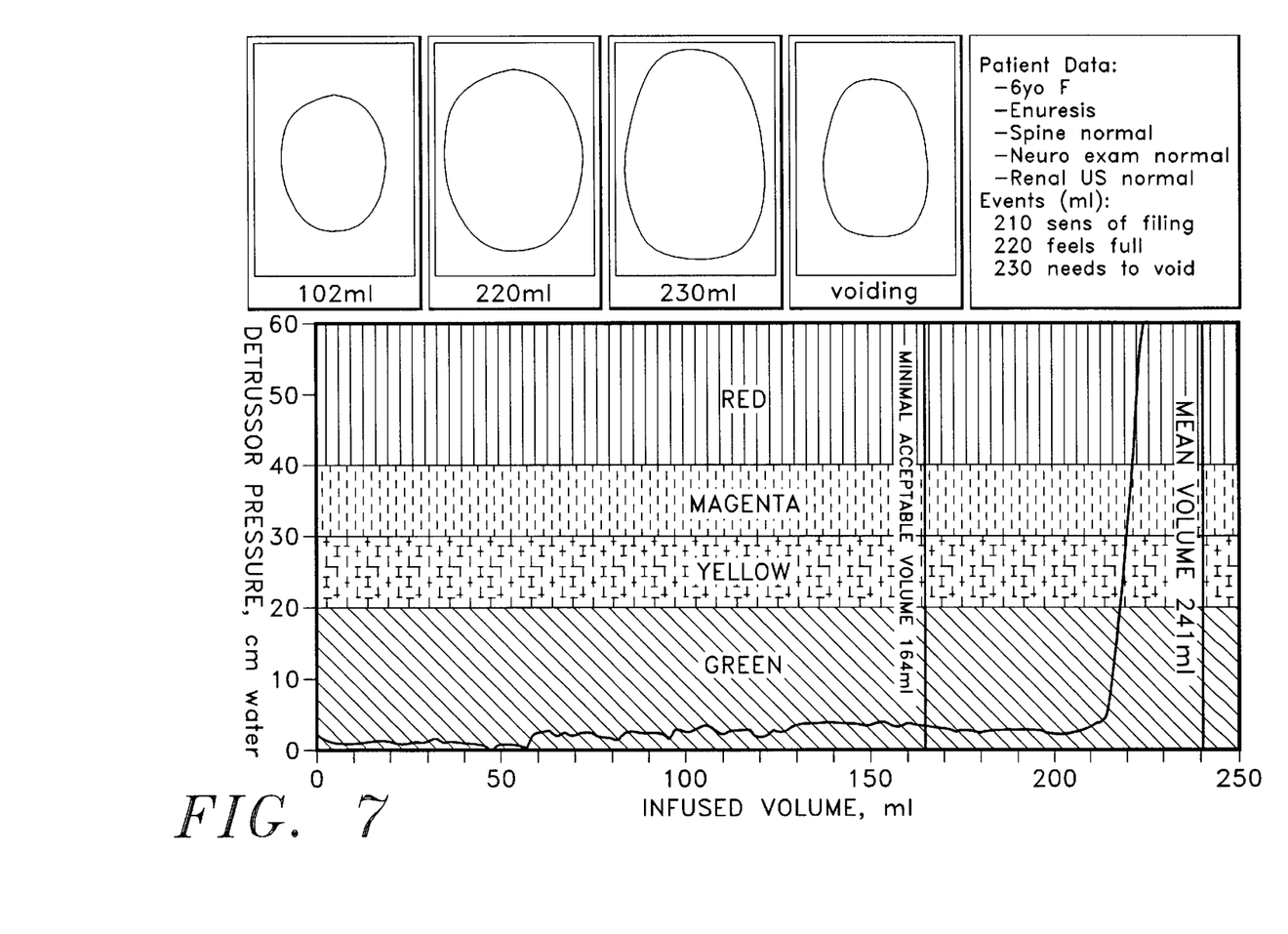
FIG. 7 is a first graphical representation of the data output in relation to volume together with x-ray representations.
Figure 8:
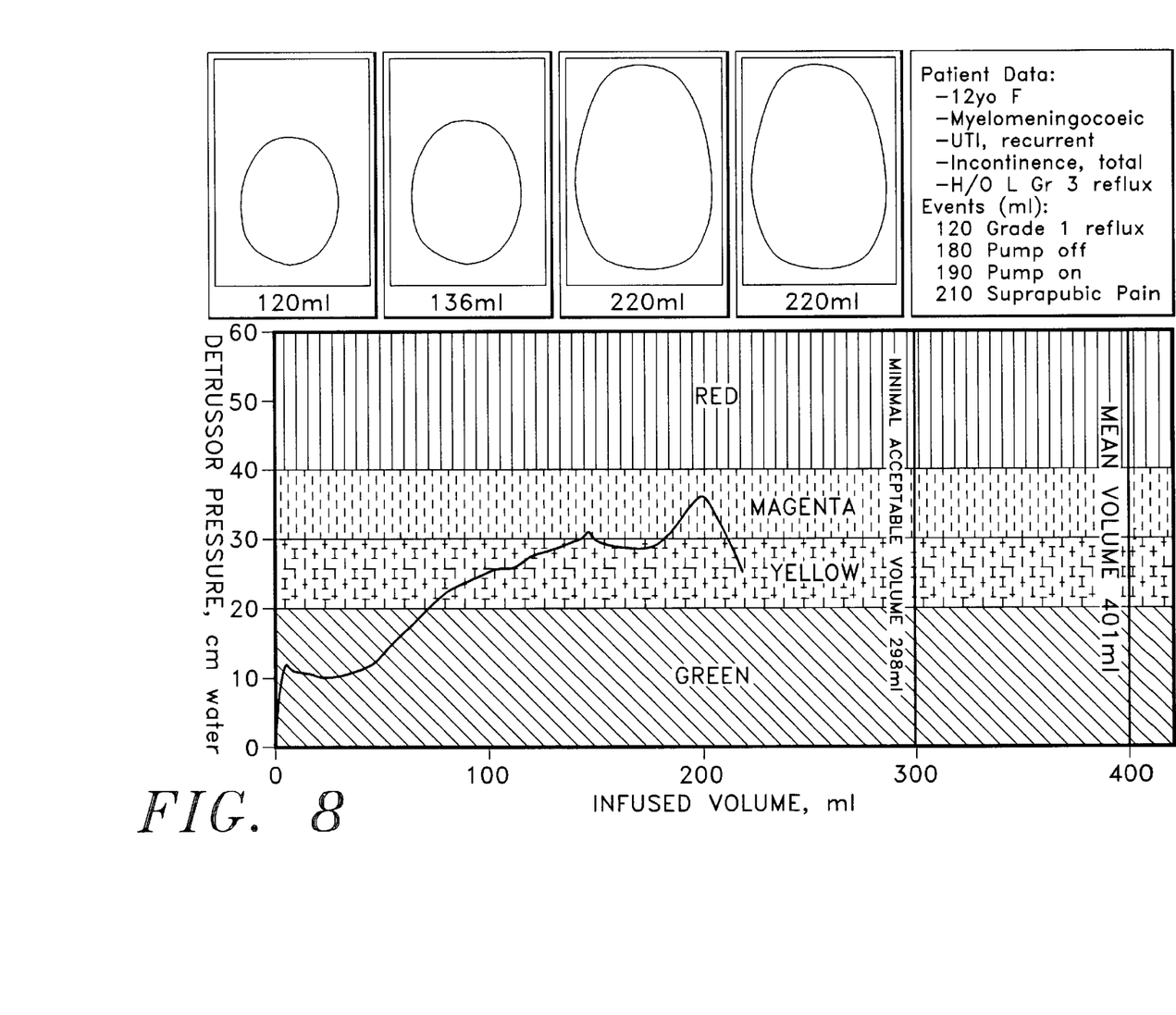
FIG. 8 is a second graphical representation of the data output in relation to volume together with x-ray representations.

These reports are shown in FIGS. 7 and 8. The report of FIG. 7 represents a normal situation, in that the pressure only increased beyond the safe level after the minimal acceptable volume was reached. The report of FIG. 8 represents an abnormal situation, in that the pressure increased beyond the safe level before the minimal acceptable volume was reached.

The Advantageous Features Include:
1. Colors add another dimension to the horizontal and vertical dimensions of a sheet of paper. Colors enable us to add additional information, in this case, the physiologic importance of the pressure.
2. The colors red, yellow and green add the characteristics of a) green indicates that the pressure is safe, b) yellow indicates that there is pending danger and predicts potential danger to the upper urinary tract, c) red indicates a high pressure and severely dangerous condition in which renal damage and destruction will occur if the pressures persist. Thus the familiar parameters of red, yellow and green are used for danger, caution and safe.
3. Pressure is plotted on the vertical axis versus volume on the horizontal axis instead of time. This allows presentation of additional information on the plot, namely the mean bladder volume. This enables the plot to comprehensively indicate the safe and unsafe pressures relative to the volume and therefore indicate comprehensively a failing or satisfactory reading from a single report.
4. Curve fitting and data analysis as well as improved accuracy of the data improves the interpretation of the data and acids to the clarity and comprehensiveness of the report.
5. X-rays, that is anatomical imaging are incorporated and keyed to the volume plot. The x-rays are taken at stages representative of different volumes of fluid in the bladder. This data can be correlated with the colored graphical data which is also plotted on a volume scale.

This simultaneous graphical display of all physiologically relevant data provide a comprehensive report that is easy to explain and is meaningful. The visual display and playback of the material in real time enables teaching and explanation to be more readily conducted.

This data output report procedure takes the urologic field from the realm of simply answering the question of what the capacity to answering the question of what the bladder can hold under safe conditions. Thus, the simultaneous imaging, color graphics and individualized patient norms provide a comprehensive and individualized graphic presentation.

Different applications of the invented system are possible. For instance, the output reporting in color can be used with other physiological data, such EKG data and other vital signs and information of the body. The scope of the invention includes applying the use of color as a dimension factor to the data thereby to enhance the information being displayed and presented.

Figure 10:
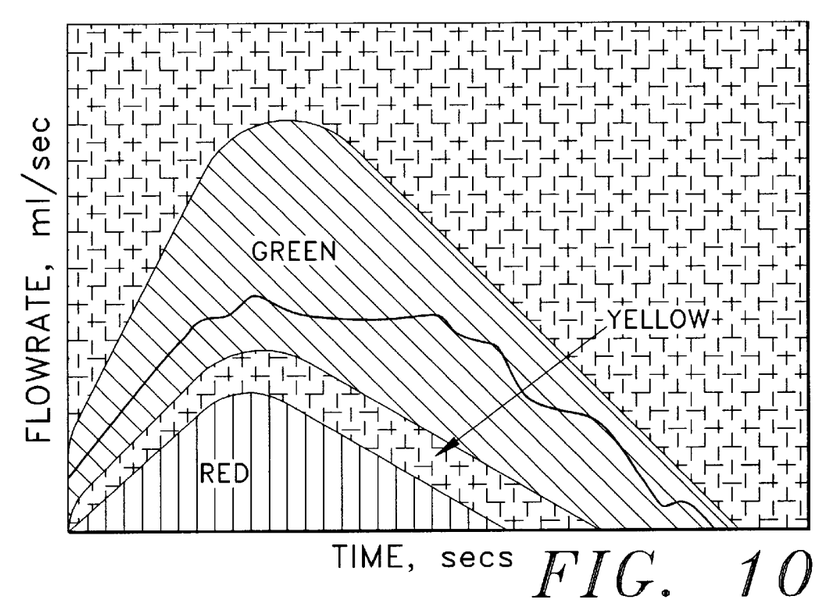
FIG. 10 is a graphical representation of the data output in relation to the uroflow which is urine rate resistance.

In regard to the uroflow application of the invention there is prepared from the literature the normal curve shape as indicated by green as well as the borderline (yellow) and unacceptable (red) regions shown in FIG. 10. These equations present the information, data, and nomographs in the literature by the shape of the curves as a mathematical function of the sex age height and weight for the specific patient, and the total, maximum flow rate and curve type for the each individual test. These equations are used in the program to prepare the plots, a typical one being shown in FIG. 10. In this figure the experimental data is shown by the dark line which is flow rate plotted versus time.

Figure 11:
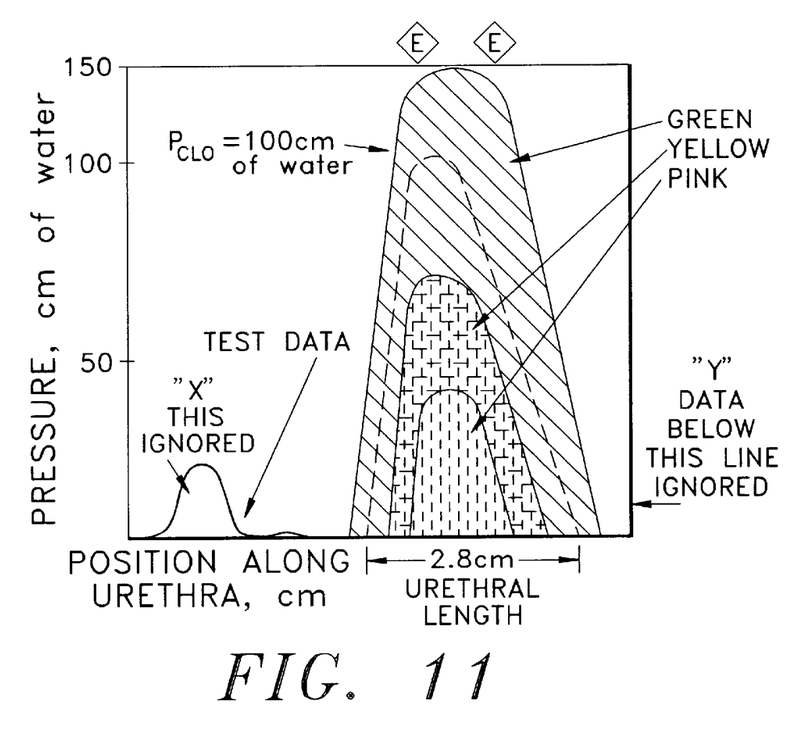
FIG. 11 is a graphical representation of the data output in relation to urethral pressure profile (UPP) measurement which is pressure versus urethral position.

FIG. 11 illustrates a UPP(Urethral Pressure Profile). In practice the urethral pressure is obtained either by measuring only the urethral pressure or by measuring both the urethral pressure and the vesicle (bladder) pressure and taking the differences to determine the net urethral pressure used in plotting the UPP. The resulting test data is analyzed from the raw pressure data as discussed under CMG above (cf FIG. 2) to give the heavy line shown in FIG. 11. In this figure the pressure is plotted versus the position of the pressure port along the length of the urethra. Event markers shown by the large E are placed on the data to indicate the approximate entry into the sphincter and the approximate exit.

The data shown by the dashed line is fit with a modification to an inverse hyperbolic curve. In this methodology artifacts in the data are ignored prior to fitting the curve fit by identifying certain data regions. The first is to ignore data that is clearly outside the region of interest indicated by the event markers as shown by the X in the figure. Note that the event markers are used only to find the key "mountain" and not the exact boundaries. Another is to ignore the data near the lower portion, typically 5% of the maximum height, that does not represent meaningful information as shown by the "Y" on the figure.

From this the closing pressure Pclo which is the maximum of the peak and the urethral length which is the intersecting of the dashed theoretical line with the base axis is obtained as indicated on the figure. Also plotted on this figure are curve shapes using the colors green, yellow and pink to indicate the acceptable, borderline and unacceptable regions for a person of this particular age, sex, height and weight. These shapes are generated by the computer program using mathematical functions which are function of sex, age, height and weight. These represent the nomographs and data in the literature.

Figure 12:
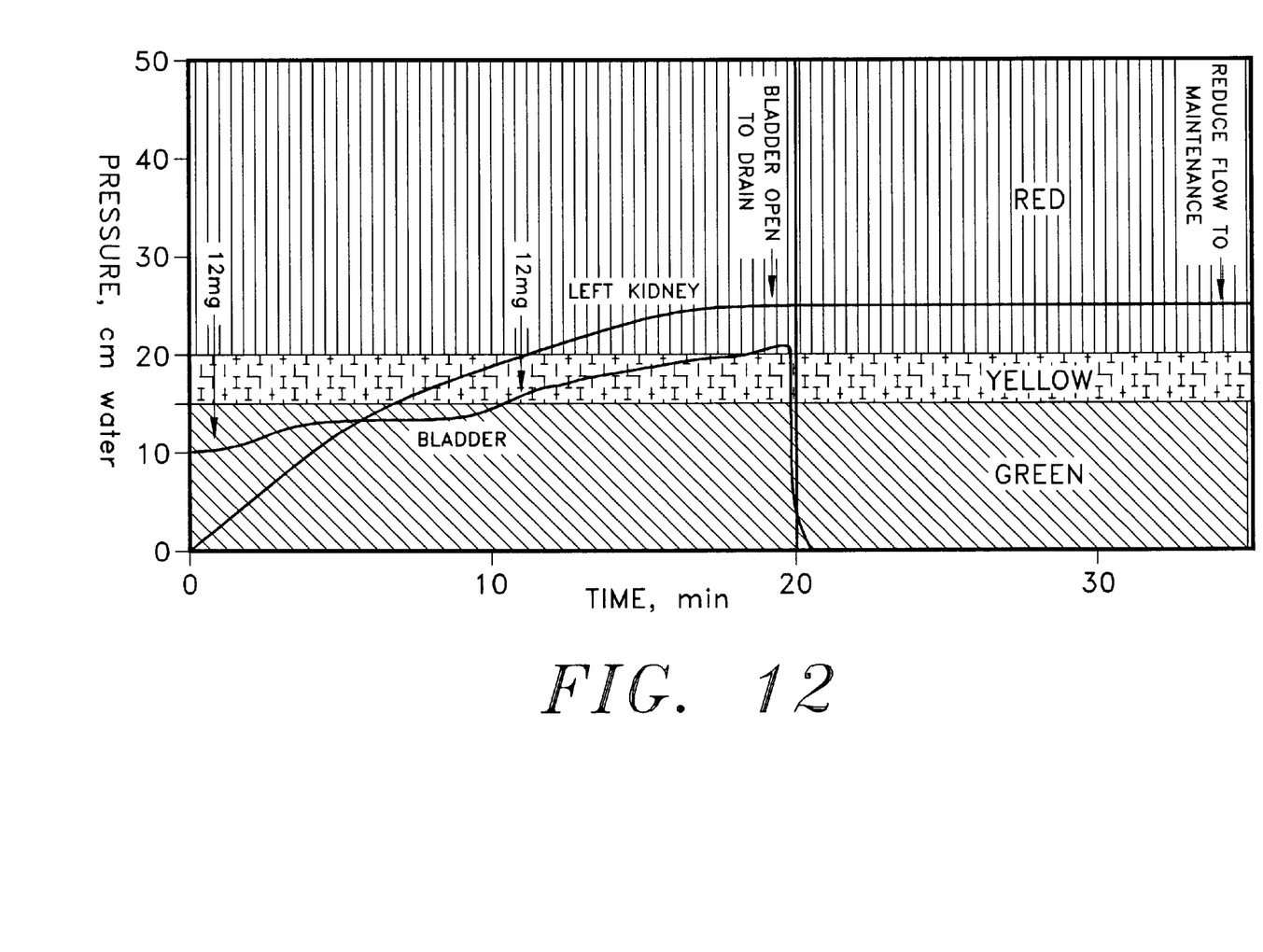
FIG. 12 is a graphical representation of the data output in relation to kidney pressure versus time.

A Whittaker/kidney test is shown in FIG. 12. This is a plot of kidney pressure during the test. The acceptable, borderline and dangerous pressure regions are shown in green, yellow and red respectively. Also shown is the bladder pressure as a dashed line. Note that there may simultaneously be one or both kidney pressures plotted versus time. In this figure only the Left kidney is shown.

While different embodiments of the invention have been shown and described, changes and modifications may be made without departing from the scope of the invention.

For example, additional pressure sensors can be used for further improvement in the data. Further although the graphical data is described as being in the two dimensional presentation format, it is also possible to have the data in three dimensions, namely where the data is resented in the x, y, and z axes.

The scope of the invention is to be determined by the following claims.

We claim:

1. A method for obtaining diagnostic test data including data output of a specific patient comprising:

representing on a single report, at least a two dimensional graphical presentation of physiological data of a patient and at least a two dimensional graphic format of data of a normal individual relative to the specific patient;

processing raw data prior to representing the physiological data on the report by smoothing the raw data prior to the representation thereby to minimize noise and provide smoothed data, and subsequently processing the smoothed data to effect curve fitting;

displaying the physiological data as a representation of urodynamic data of the patient, such representation being a presentation including bladder volume, a pressure characteristic, and the physiological data being represented as a function of bladder volume; and representing as an output, the urodynamic data and X-ray imaging data.

2. A method as claimed in claim 1 including the incorporation of zones as a dimension to the graphical presentation of the physiological data of the normal individual, such normal data being in horizontal and vertical dimensions.

3. A method as claimed in claim 2 wherein the zones are colors, the colors being selectively green, yellow and red.

4. A method as claimed in claim 2 including filtering the raw data, such that when operating under at least one of the conditions that, when a rate of rise of pressure exceeds a pre-set value the raw data obtained under such conditions is discarded, or when a pressure exceeds an average pressure that had been maintained over a recent time period by more than a pre-set amount, the raw data obtained under such conditions is discarded.

5. A method as claimed in claim 2 including obtaining a detrusor pressure, such detrusor pressure being obtained by first smoothing a bladder pressure data and a rectal pressure data obtained from a measurement of pressure in the abdomen and then subsequently performing a subtraction of such bladder pressure and rectal pressure to obtain the detrusor pressure.

6. A method as claimed in claim 5 wherein the graphical presentation contains two detrusor pressures, one detrusor pressure being the difference between a time spaced average data points of the bladder and rectal pressures and the other pressure being obtained by subtracting curve fitted rectal and bladder pressures.

7. A method as claimed in claim 1 including obtaining the raw data through analog measurement means, an analog to digital data conversion means for converting the raw data to a digital input, a software program for reading the digital input, means for sampling the converted raw data for minimizing artifacts in the converted raw data that are substantially non physiological while retaining the physiological data.

8. A method as claimed in claim 1 including providing the colors of green, yellow and red as background on which the physiological data is displayed, and the presentation includes bladder capacity information as vertical lines, and pressure as horizontal colored areas.

9. A method as claimed in claim 1 including analyzing in real time the collected raw data which has been processed, and analyzing the processed data in relation to data obtained after obtaining the collected raw data, and including taking the collected raw data from the patient and calculating characteristics for displaying the physiological data.

10. A method as claimed in claim 1 including directing a catheter into a bladder, including filling the bladder with fluid, and measuring the bladder pressure, and locating in the abdomen a sensor for measuring pressure in the abdomen in the area outside the bladder.

11. A method as claimed in claim 1 including rendering the representation of urodynamic data as an output display reported in relation to color, the color being selectively representative of physiological significant data.

12. A method as claimed in claim 1 wherein the diagnostic test data output of a specific patient is related relative to representative data of a normal individual.

13. A method for obtaining diagnostic test data including data output for a patient comprising:

representing on a single report, a graphical presentation of physiological data of the patient and imaging data of the patient;

processing raw data prior to representing the physiological data on the report by smoothing the raw data prior to the representation thereby to minimize noise and provide smoothed data, and subsequently processing the smoothed data to effect curve fitting;

displaying the physiological data as a representation of urodynamic data of the patient, such representation being a presentation including bladder volume, a pressure characteristic, and the physiological data being represented as a function of bladder volume; and representing as an output, the urodynamic data and X-ray imaging data.

14. A method for obtaining urodynamics diagnostic test data of a patient comprising representing the production of a graphical presentation report of physiological data of a specific patient, and imaging data of internal anatomical features of the patient, including incorporating zones as a dimension to the graphical presentation of data of a normal individual relative to the physiological data of specific patient data, such normal data being portrayed in horizontal and vertical dimensions;

analyzing in real time the physiological data and further analyzing the collected data in relation to data obtained after obtaining the physiological data;

processing and presenting the, including taking the patient data and calculating the characteristics for the display; and displaying the physiological data as a presentation, such presentation including bladder capacity information, and a pressure characteristic, and additionally displaying the imaging data.

15. A method as claimed in claim 14 wherein the zones are colors, the colors being selectively green, yellow and red.

16. A method as claimed in claim 15 including providing the colors of green, yellow and red as background on which the physiological data is displayed, and the presentation includes bladder capacity information as vertical lines, and pressure as horizontal lines.

17. A method as claimed in claim 14 wherein the diagnostic test data output of a specific patient is related relative to representative data of a normal individual.

18. A method for obtaining urodynamic diagnostic test data comprising representing data output of a patient as a graphical presentation report of the test data of the patient and including incorporating different discrete color zones as a background dimension to the graphical presentation of data of a relatively normal individual in horizontal and vertical dimensions, obtaining detrusor pressures, one detrusor pressure being the difference between data points of the bladder and rectal pressures and the other being obtained by subtracting rectal and bladder pressures, including displaying as the data, bladder capacity information, pressure characteristics, and data as a function of bladder volume; and relating data output of a specific patient relative to urodynamic data of a normal individual.

* * * * *